US012582397B2

(12) United States Patent
Ding et al.

(10) Patent No.: US 12,582,397 B2
(45) Date of Patent: Mar. 24, 2026

(54) SURGICAL INSTRUMENT WITH LOCKOUT FEATURES

(71) Applicant: Cilag GmbH International, Zug (CH)

(72) Inventors: Sheng Ding, Shanghai (CN); Chunchun Liu, Shanghai (CN); Hong Xiangchun, Shanghai (CN)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/851,277

(22) PCT Filed: Apr. 5, 2023

(86) PCT No.: PCT/IB2023/053469
§ 371 (c)(1),
(2) Date: Sep. 26, 2024

(87) PCT Pub. No.: WO2023/194928
PCT Pub. Date: Oct. 12, 2023

(65) Prior Publication Data
US 2025/0228559 A1     Jul. 17, 2025

(30) Foreign Application Priority Data
Apr. 8, 2022     (CN) ......................... 202210369813.2

(51) Int. Cl.
| A61B 17/072 | (2006.01) |
| A61B 90/00 | (2016.01) |
| A61B 17/00 | (2006.01) |

(52) U.S. Cl.
CPC ............ *A61B 17/072* (2013.01); *A61B 90/03* (2016.02); *A61B 2017/00477* (2013.01); *A61B 2017/07271* (2013.01); *A61B 2090/034* (2016.02)

(58) Field of Classification Search
CPC ......................... A61B 17/07207; A61B 90/03
See application file for complete search history.

(56) References Cited

U.S. PATENT DOCUMENTS

| 4,354,628 | A | 10/1982 | Green |
| 4,527,724 | A | 7/1985 | Chow et al. |
| 4,568,009 | A | 2/1986 | Green |
| 4,573,622 | A | 3/1986 | Green et al. |

(Continued)

FOREIGN PATENT DOCUMENTS

| CN | 102835983 B | 8/2016 |
| EP | 0537572 B1 | 6/1999 |

(Continued)

OTHER PUBLICATIONS

International Search report and Written Opinion dated Jul. 12, 2023, for International Application No. PCT/IB2023/053469, 9 pages.

(Continued)

*Primary Examiner* — Nathaniel C Chukwurah
(74) *Attorney, Agent, or Firm* — FBT Gibbons LLP

(57) ABSTRACT
A surgical instrument includes a lockout assembly that can be unlocked by a surgical staple cartridge. The lockout assembly prevents a pair of closure plates and a firing bar of the surgical instrument from advancing distally when in a locked position, and allows the pair of closure plates and the firing bar to advance distally when in an unlocked position.

11 Claims, 10 Drawing Sheets

(56)                    References Cited

U.S. PATENT DOCUMENTS

| | | | |
|---|---|---|---|
| 4,585,153 | A | 4/1986 | Failla |
| 4,715,520 | A | 12/1987 | Roehr et al. |
| 4,805,523 | A | 2/1989 | Rothfuss |
| 4,805,823 | A | 2/1989 | Rothfuss |
| 4,848,637 | A | 7/1989 | Pruitt |
| 4,930,503 | A | 6/1990 | Pruitt |
| 5,439,155 | A | 8/1995 | Viola |
| 5,462,215 | A | 10/1995 | Viola et al. |
| 5,547,117 | A | 8/1996 | Hamblin et al. |
| 5,641,111 | A | 6/1997 | Ahrens et al. |
| 5,810,240 | A | 9/1998 | Robertson |
| 5,919,198 | A | 7/1999 | Graves, Jr. et al. |
| 6,805,273 | B2 | 10/2004 | Bilotti et al. |
| 6,817,508 | B1 | 11/2004 | Racenet et al. |
| 8,328,064 | B2 | 12/2012 | Racenet et al. |
| 11,202,628 | B2 | 12/2021 | Posey et al. |
| 2004/0084505 | A1 | 5/2004 | Bilotti et al. |
| 2005/0139629 | A1* | 6/2005 | Schwemberger .... A61B 17/072 227/19 |
| 2011/0226837 | A1 | 9/2011 | Baxter, III et al. |
| 2013/0206813 | A1 | 8/2013 | Nalagatla |
| 2015/0119904 | A1 | 4/2015 | Ji et al. |
| 2017/0281177 | A1* | 10/2017 | Harris ................ A61B 17/0686 |
| 2020/0205810 | A1 | 7/2020 | Posey et al. |
| 2020/0205811 | A1 | 7/2020 | Posey et al. |
| 2020/0337699 | A1 | 10/2020 | Rector et al. |
| 2020/0337700 | A1* | 10/2020 | Hontz .................. A61B 17/072 |
| 2021/0186495 | A1 | 6/2021 | Shelton, IV et al. |
| 2022/0000479 | A1 | 1/2022 | Shelton, IV et al. |
| 2022/0142641 | A1 | 5/2022 | Wang |
| 2024/0225642 | A1 | 7/2024 | Ren et al. |
| 2025/0049436 | A1 | 2/2025 | Wang |
| 2025/0195065 | A1 | 6/2025 | Yang et al. |
| 2025/0204912 | A1 | 6/2025 | Yang et al. |
| 2025/0213248 | A1 | 7/2025 | Zhang et al. |
| 2025/0213250 | A1 | 7/2025 | Ding et al. |
| 2025/0255605 | A1 | 8/2025 | Yang et al. |

FOREIGN PATENT DOCUMENTS

| | | | |
|---|---|---|---|
| EP | 1550411 | A1 | 7/2005 |
| EP | 1552791 | A1 | 7/2005 |
| EP | 1552791 | B1 | 6/2009 |
| EP | 1550411 | B1 | 7/2009 |
| EP | 3225179 | A1 | 10/2017 |
| EP | 3476310 | | 5/2019 |
| EP | 3225179 | B1 | 4/2020 |
| EP | 3636166 | A2 | 4/2020 |
| EP | 3673826 | A1 | 7/2020 |
| EP | 3730068 | A1 | 10/2020 |
| EP | 3730069 | A1 | 10/2020 |
| EP | 3730070 | A1 | 10/2020 |
| EP | 3730069 | B1 | 7/2023 |
| EP | 3730068 | B1 | 9/2023 |
| EP | 3636166 | B1 | 3/2024 |
| WO | 2021/168704 | A1 | 9/2021 |
| WO | 2021/168726 | A1 | 9/2021 |

OTHER PUBLICATIONS

International Search Report and Written Opinion dated Jul. 4, 2023 for Application No. PCT/IB2023/053467, 9 pages.
International Search Report and Written Opinion dated Jul. 21, 2023 for Application No. PCT/IB2023/053476, 9 pages.
International Search Report and Written Opinion dated Jun. 29, 2023 for Application No. PCT/IB2023/053477, 10 pages.
International Search Report and Written Opinion dated Jul. 5, 2023 for Application No. PCT/IB2023/053478, 9 pages.
International Search Report and Written Opinion dated Jul. 5, 2023 for Application No. PCT/IB2023/053481, 10 pages.
International Search Report and Written Opinion dated Jul. 14, 2023 for Application No. PCT/IB2023/053483, 12 pages.

* cited by examiner

SURGICAL INSTRUMENT WITH LOCKOUT FEATURES

FIELD

The present disclosure relates to the field of surgical instruments, in particular to a surgical instrument with lockout features.

BACKGROUND

A surgical instrument such as surgical stapler/anastomat is usually used to deploy staples into tissue for reducing or eliminating tissue bleeding, for example, it is necessary to seal the tissue as the tissue being cut in order to promote healing. A surgical stapler/anastomat (such as a linear stapler/anastomat, a right-angle stapler/anastomat) may comprise an end effector assembly having a staple cartridge portion and a staple anvil portion, the end effector assembly is configured to secure the tissue between the staple cartridge portion and the staple anvil portion, wherein the staple cartridge portion comprises a replaceable staple cartridge configured to removably store surgical staples therein, and the staple anvil portion comprises staple forming pockets for forming the staples. Such surgical stapler/anastomat generally comprises a closure system that moves one of the staple cartridge portion and the staple anvil portion relative to the other, and a firing bar for firing the staples.

During use, the staple cartridge portion and the staple anvil portion of the end effector assembly of the surgical stapler/anastomat are closed to form a close configuration, in order to capture the tissue between the staple cartridge portion and the staple anvil portion. Then, the firing bar pushes the staples to deploy from the staple cartridge, pass through the tissue, and to be formed against the staple forming pockets of the staple anvil portion, so as to seal tissue layers together. The staples are usually deployed in form of several staple lines or staple rows in order to secure the tissue layers together more reliably. The end effector assembly may comprise or not comprise a cutting member that can be advanced between the staple lines in order to cut the tissue after the tissue layers have been sealed together.

In one aspect, a closing action for closing the end effector assembly and a firing action for firing the staples may be not allowed in the case of no surgical staple cartridge being installed in the surgical instrument, which may otherwise damage the surgical instrument or cause misoperation.

In another aspect, the closing action for closing the end effector assembly and the firing action for firing the staples may be not allowed in the case of a spent surgical staple cartridge being installed in the surgical instrument, which may otherwise damage the surgical instrument or cause misoperation.

In a further aspect, the staple cartridges and the surgical instruments usually come in a variety of models for different tissue sites and situations. A certain model of the staple cartridge may be used for one or more models of surgical instruments. In the case that an incompatible staple cartridge is installed in the surgical instrument, the closing action for closing the end effector assembly and the firing action for firing the staples may be not allowed, which may otherwise affect the sealing quality of tissue, cause the surgical instrument to malfunction, or even damage the surgical instrument and staple cartridge.

Therefore, a staple cartridge with lockout features is needed to avoid the above situation.

SUMMARY

The present disclosure provides a surgical instrument with lockout features, wherein the lockout features can lock the closure plates and firing bar of the surgical instrument in the case of the surgical instrument being not installed with a surgical staple cartridge (of a compatible model) and in the case of a spent surgical staple cartridge being installed, so as to prevent the closing of an end effector assembly and the firing of staples.

The present disclosure provides a surgical instrument, which comprises a handle assembly positioned proximally, a shaft assembly extending distally from the handle assembly, and an end effector assembly coupled to the handle assembly via the shaft assembly and configured to be manipulated by the handle assembly to transit between an open configuration and a close configuration. The end effector assembly comprises a pair of hook-shaped members; a pair of closure plates positioned between the pair of hook-shaped members, the pair of closure plates being configured to be manipulated by the handle assembly to advance distally so as to convert the end effector assembly from the open configuration to the close configuration; a firing bar positioned between the pair of closure plates, the firing bar being configured to be manipulated by the handle assembly to advance distally; and a lockout assembly, the lockout assembly being pivotally mounted on the pair of closure plates and positioned therebetween, and being configured to pivot between a locked position in which the lockout assembly prevents the pair of closure plates and the firing bar from advancing distally, and an unlocked position in which the lockout assembly allows the pair of closure plates and the firing bar to advance distally.

According to a preferred embodiment, the lockout assembly comprises a lockout member pivotably mounted between the pair of closure plates via a pivot, and a spring member configured to bias the lockout member towards the locked position.

According to a preferred embodiment, the lockout member comprises a first hook-shaped arm extending distally and a second hook-shaped arm extending proximally, when the lockout member is in the locked position, the first hook-shaped arm prevents the firing bar from advancing distally, and the second hook-shaped arm prevents the pair of closure plates from advancing distally; and when the lockout member pivots to the unlocked position, the first hook-shaped arm allows the firing bar to advance distally, and the second hook-shaped arm allows the pair of closure plates to advance distally.

According to a preferred embodiment, the first hook-shaped arm has an end which is upwardly curved, and the second hook-shaped arm has an end which is downwardly curved, and when the lockout member is in the locked position, the end of the first hook-shaped arm engages with the firing bar or is positioned at a distal side of the firing bar to prevent the firing bar from advancing distally, and the end of the second hook-shaped arm engages with a pin fixed between the pair of hook-shaped members or positioned at a proximal side of the pin to prevent the pair of closure plates from advancing distally; and when the lockout member is in the unlocked position, the end of the first hook-shaped arm disengages from the firing bar or is no longer positioned at the distal side of the firing bar so as to allow the firing bar to advance distally, and the end of the second hook-shaped arm disengages from the pin or is no longer positioned at the proximal side of the pin so as to allow the pair of closure plates to advance distally.

According to a preferred embodiment, the pair of closure plates are configured to removably hold a surgical staple cartridge which comprises a staple driver configured to be pushed distally by the firing bar to move from an unfired position to a fired position, and when the surgical staple cartridge is installed in place between the pair of closure plates along an installation direction of the surgical staple cartridge, the first hook-shaped arm is configured to be engaged by the staple driver in the unfired position to pivot the lockout member towards the unlocked position, and the first hook-shaped arm is configured to not engage with the staple driver in the fired position so as to keep the lockout member in the locked position.

According to a preferred embodiment, top ends of the pair of closure plates are respectively provided with notches, each notch being configured to receive a corresponding protrusion provided on a surgical staple cartridge which is compatible with the surgical instrument, so as to allow the surgical staple cartridge which is compatible with the surgical instrument to be installed in place between the pair of closure plates.

According to a preferred embodiment, inner sides of the pair of closure plates are provided with one or more ribs extending along the installation direction of the surgical staple cartridge, and the one or more ribs are configured to be received in corresponding slots provided on the surgical staple cartridge which is compatible with the surgical instrument.

According to a preferred embodiment, the lockout member further comprises a stepped portion located between the first hook-shaped arm and the second hook-shaped arm, and a distal-facing surface of a first end of the spring member abuts against the stepped portion, and a second end of the spring member is fixed at any one of the hook-shaped members, the closure plates and the firing bar, and a proximal-facing surface of a portion of the spring member between the first end and the second end abuts against the pivot.

According to a preferred embodiment, the spring member has a slot extending in a longitudinal direction of the spring member, and the lockout member is adapted to passes through the slot such that the first hook-shaped arm is positioned distal to the spring member and the second hook-shaped arm is positioned proximal to the spring member.

According to a preferred embodiment, a dimension of the notch along the installation direction of the surgical staple cartridge is associated with the locked position and the unlocked position of the lockout member.

According to a preferred embodiment, the notch has a substantially triangular profile, and wherein one vertex of the triangular profile faces towards the installation direction of the surgical staple cartridge.

BRIEF DESCRIPTION OF THE DRAWINGS

The present disclosure and its features and advantages will be better understood with reference to the following description of exemplary embodiments of the present disclosure in conjunction with the accompanying drawings. In the following description and drawings, similar components are indicated with similar reference signs. The figures are not necessarily drawn to scale, and for the sake of clarity and conciseness, some parts may be omitted, and some figures may be drawn in an exaggerated or sketchy way.

Figure 1:
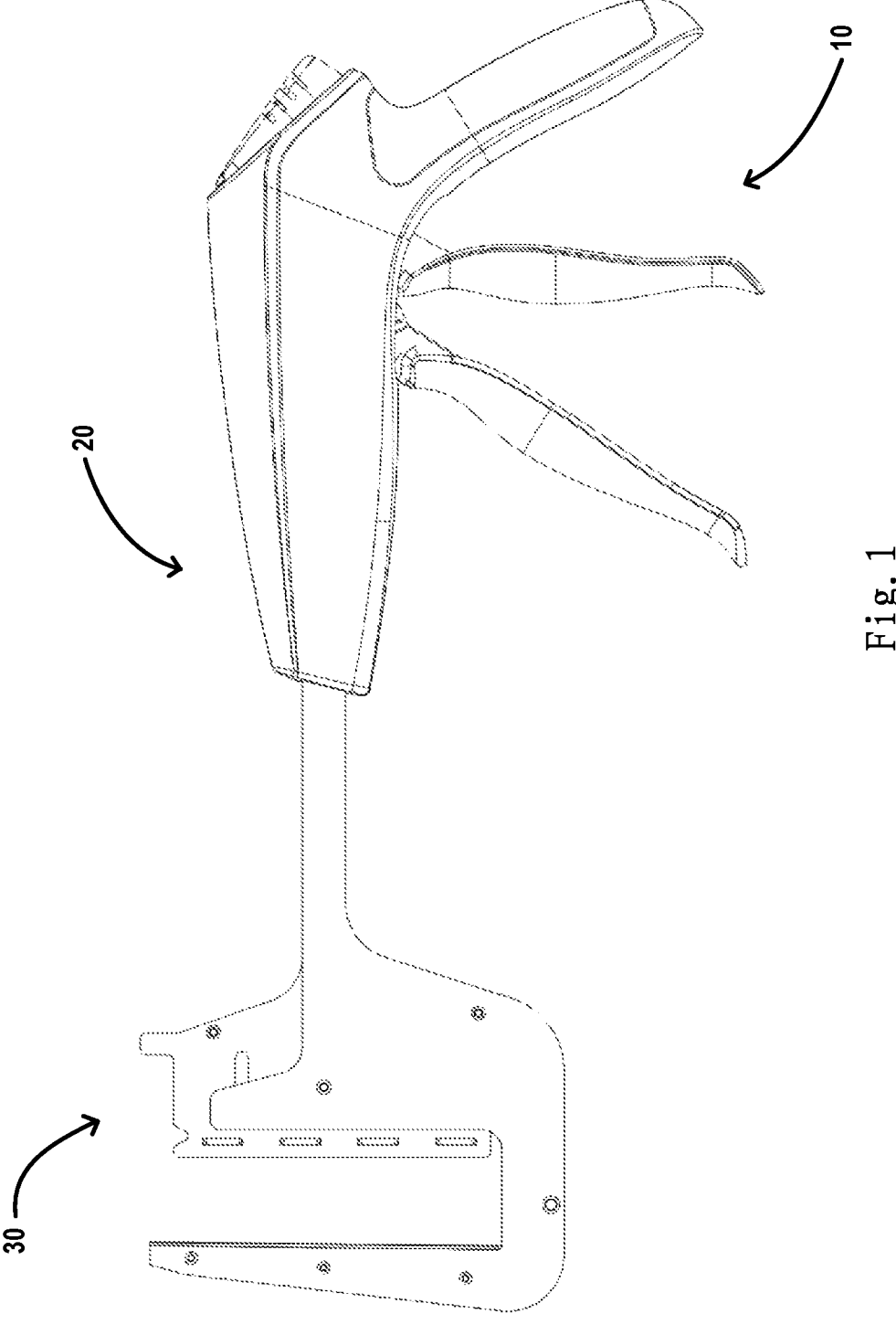
Figure 2:
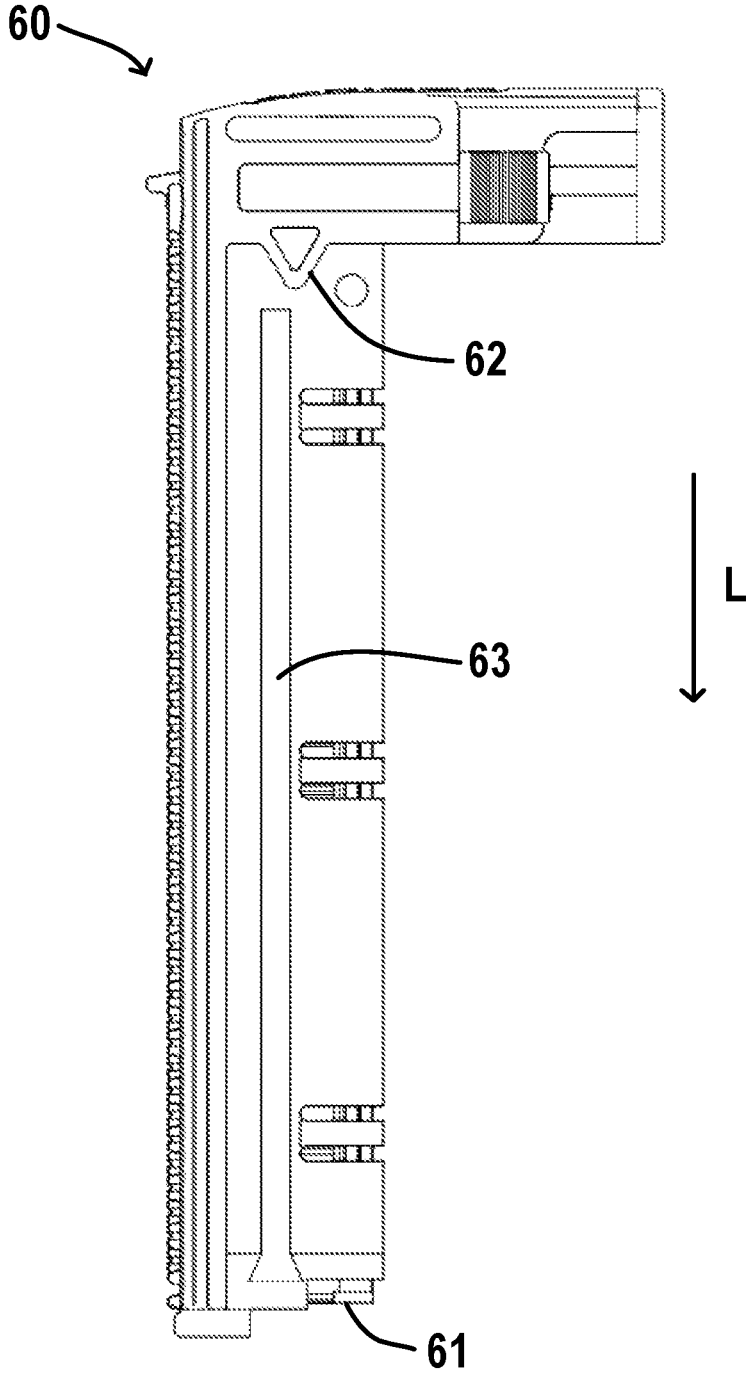
Figure 3:
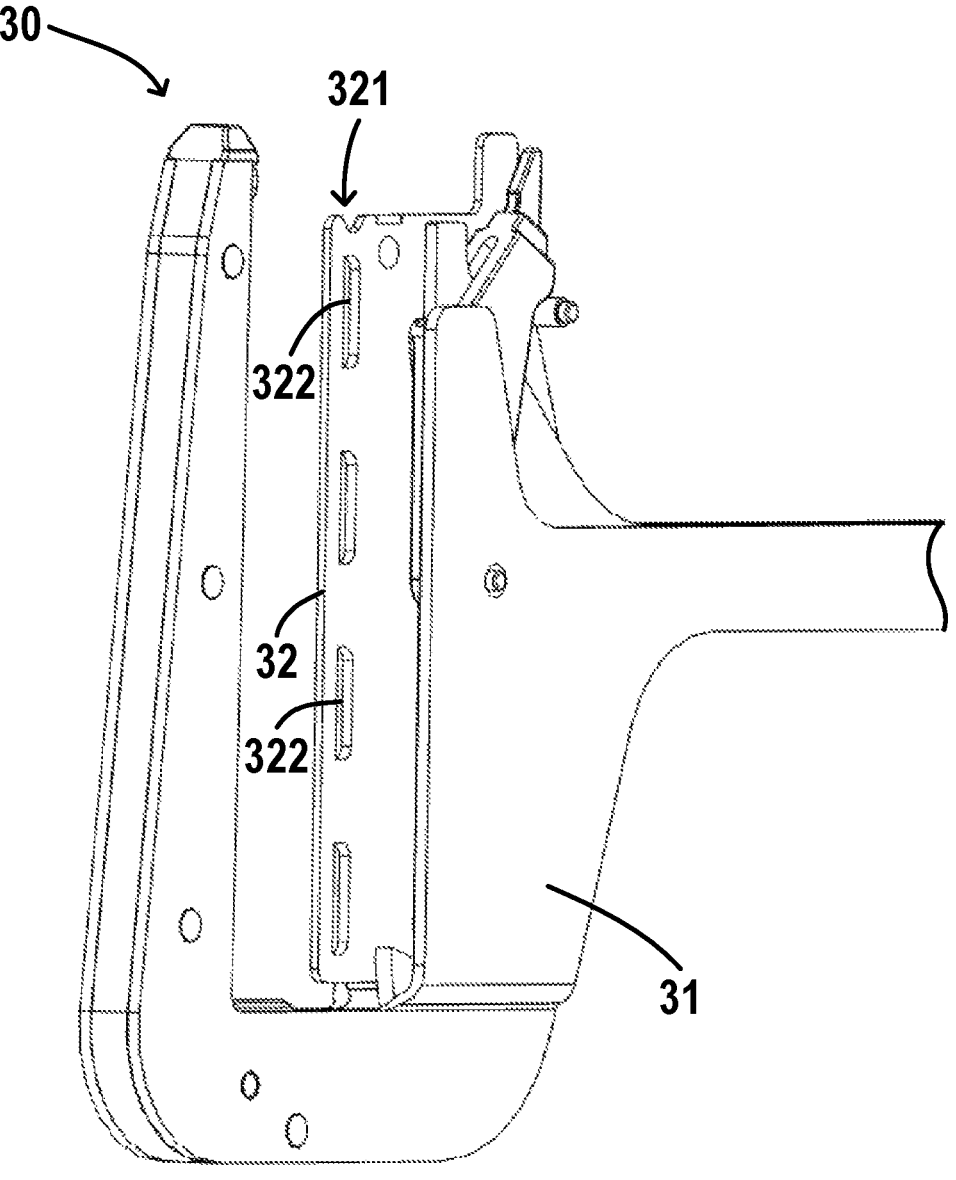
Figure 4:
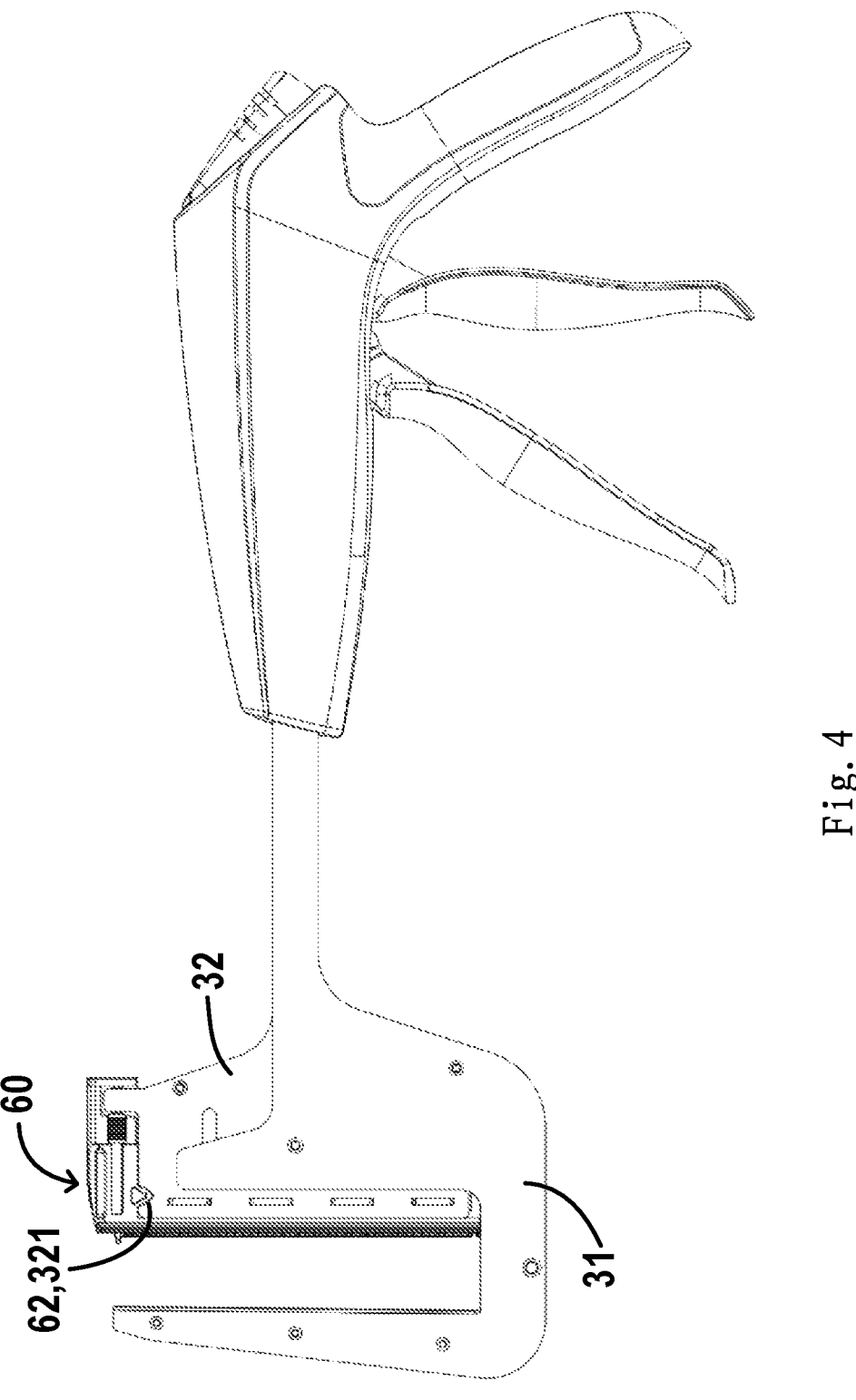
Figure 5:
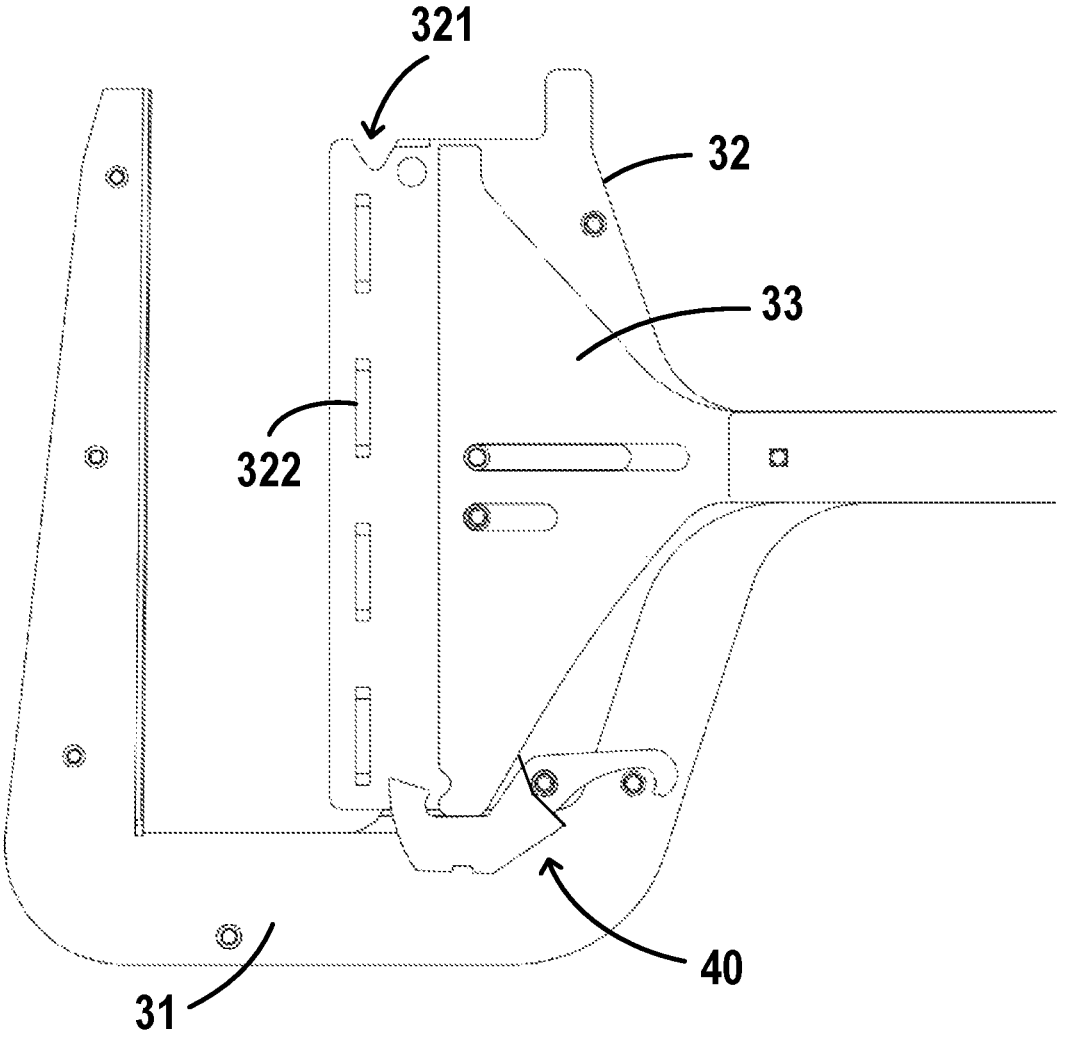
Figure 6:
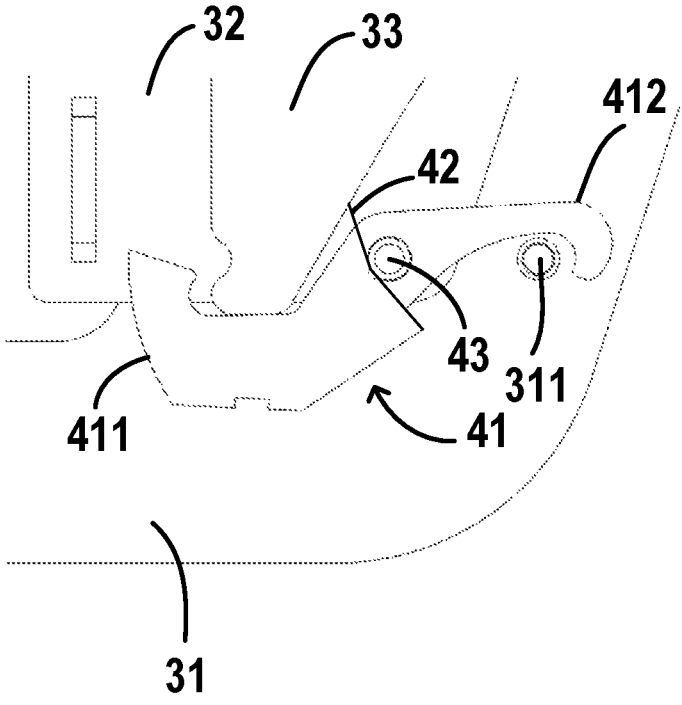
Figure 7:
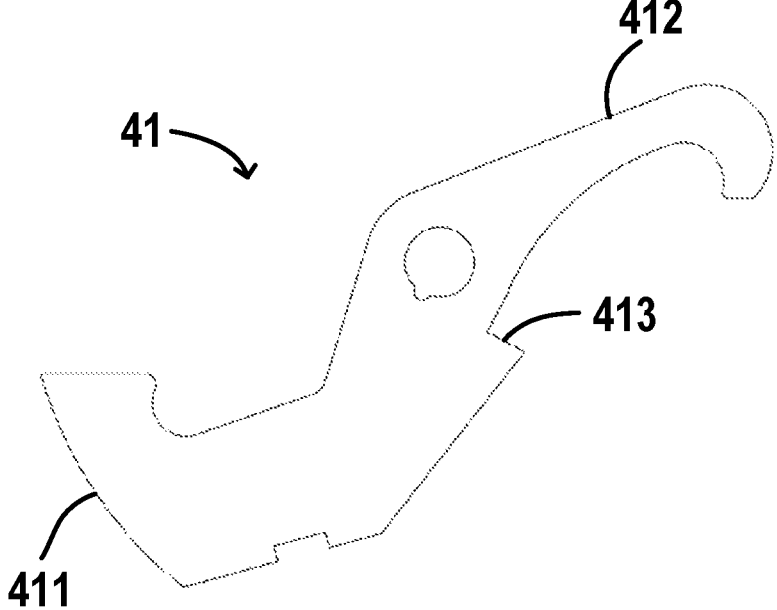
Figure 8:
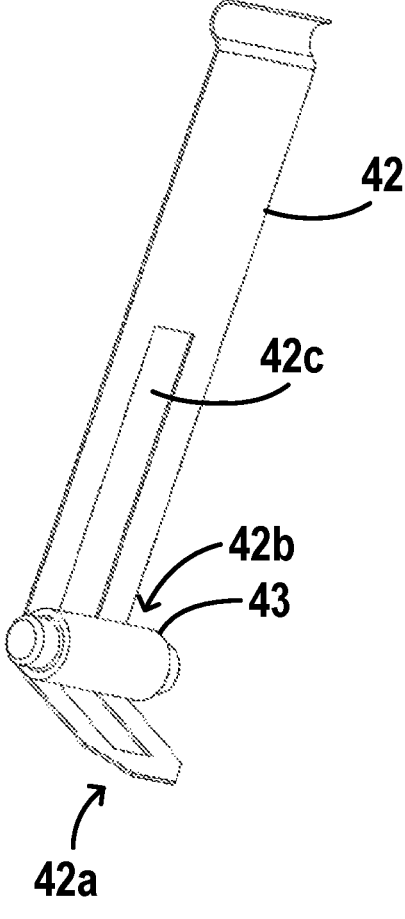
Figure 9:
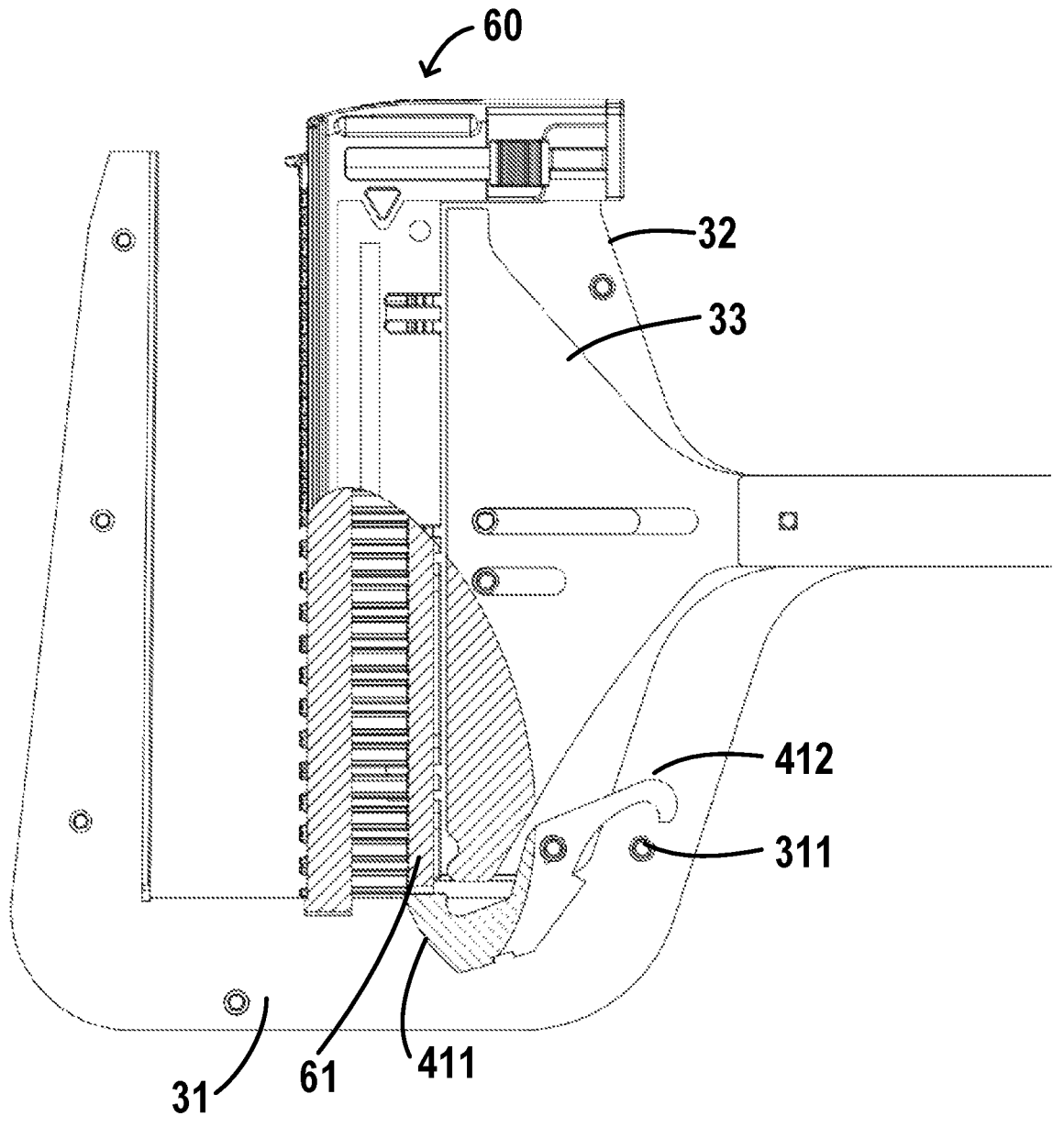
Figure 10:
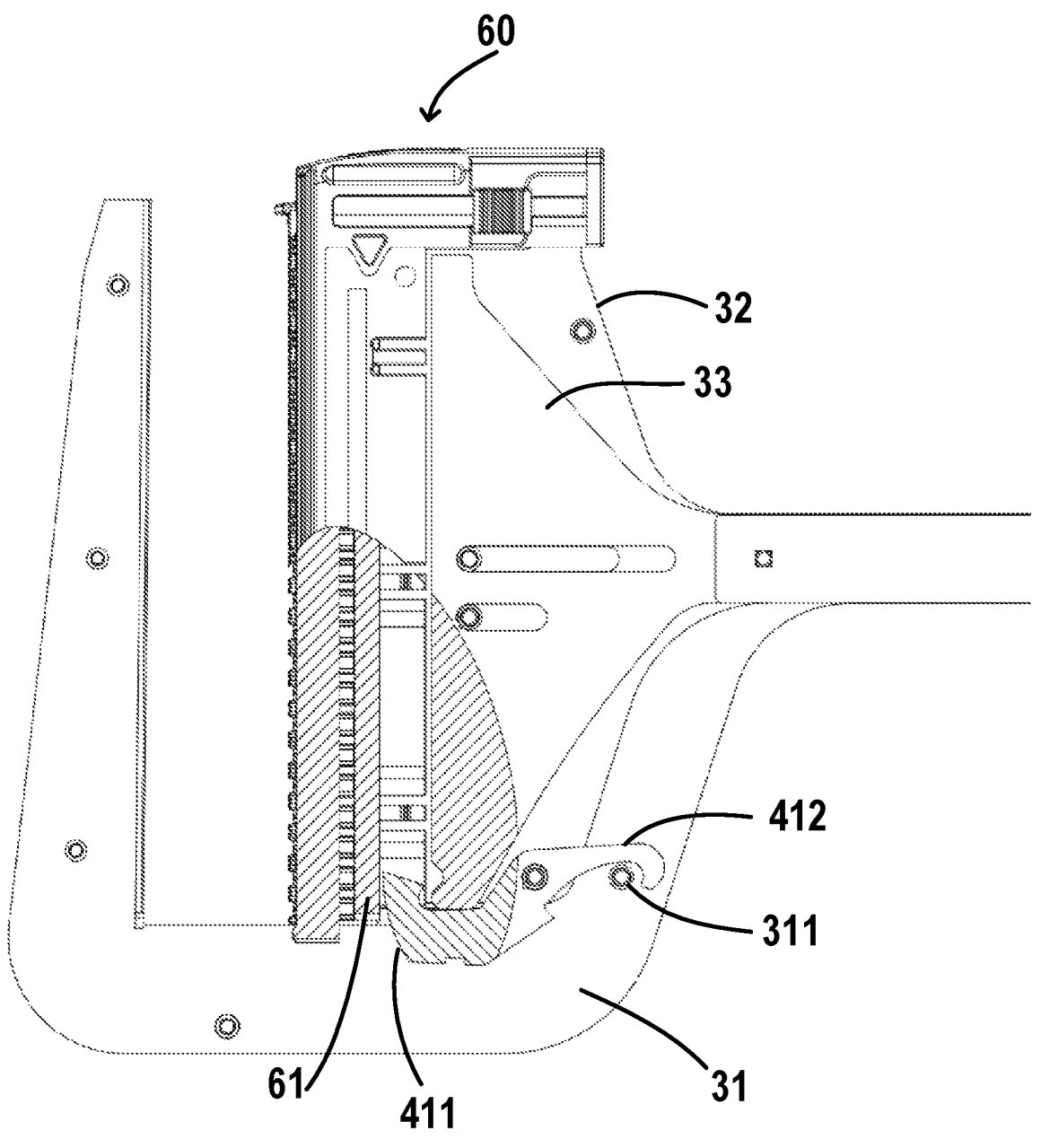

FIG. 1 exemplarily shows a side view of a surgical instrument according to the present disclosure;

FIG. 2 exemplarily shows a side view of a surgical staple cartridge according to the present disclosure;

FIG. 3 exemplarily shows a partial enlarged view of an end effector portion of the surgical instrument shown in FIG. 1, in which some components are omitted;

FIG. 4 exemplarily shows a side view of the surgical instrument in FIG. 1 installed with the surgical staple cartridge in FIG. 2;

FIG. 5 exemplarily shows a partial enlarged view of the end effector portion of the surgical instrument of FIG. 1, in which some components are omitted;

FIG. 6 exemplarily shows a partial enlarged view of the lockout assembly in FIG. 5;

FIG. 7 exemplarily shows a lockout member of the lockout assembly according to the present disclosure;

FIG. 8 exemplarily shows a spring member of the lockout assembly according to the present disclosure;

FIG. 9 exemplarily shows a partial enlarged view of the end effector portion of the surgical instrument with the lockout assembly in an unlocked position, in which some components are omitted;

FIG. 10 exemplarily shows a partial enlarged view of the end effector portion of the surgical instrument installed with a spent surgical staple cartridge, in which some components are omitted.

DETAILED DESCRIPTION OF EMBODIMENTS

Next, exemplary embodiments of the present disclosure will be described in detail with reference to the accompanying drawings. Described herein are merely exemplary embodiments in accordance with the present disclosure, and those skilled in the art will envisage other ways to implement the present disclosure on the basis of the exemplary embodiments described herein, which also fall within the scope of the present disclosure.

In the following detailed description, "proximal" refers to a direction close to an operator of the surgical instrument, and "distal" refers to a direction away from the operator of the surgical instrument.

FIG. 1 exemplarily shows a surgical instrument according to the present disclosure, which comprises a proximally positioned handle assembly 10, a shaft assembly 20 extending distally from the handle assembly 10, and an end effector assembly 30 coupled to the handle assembly 10 via the shaft assembly 20. An operator may control the end effector assembly 30 to switch between an open configuration and a close configuration and control the firing of staples by operating the handle assembly 10. The end effector assembly 30 shown in FIG. 1 is in the open configuration, and a surgical staple cartridge 60 shown in FIG. 2 can be installed in the surgical instrument of FIG. 1.

Referring to FIG. 3 to FIG. 8, the end effector assembly 30 comprises a pair of hook-shaped members 31, a pair of closure plates 32 positioned between the pair of hook-shaped members 31, and a firing bar 33 positioned between the pair of closure plates 32. The hook-shaped member 31 is substantially U-shaped or C-shaped, and is mainly used for carrying other components. The closure plate 32 is used to hold the surgical staple cartridge, which can be manipulated by the handle assembly 10 to advance distally with the surgical staple cartridge so as to render the end effector assembly 30 to be in a close configuration. The firing bar 33 may be manipulated by the handle assembly 10 to advance distally and then fire the staples in the surgical staple cartridge. Specifically, the surgical staple cartridge comprises a staple driver 61 for pushing the staples to fire from the staple cartridge. In an unused staple cartridge (see FIG. 2 and FIG. 9), the staple driver 61 is in an initial position (or an unfired position) and the staples are accommodated in the staple cartridge; and in a spent staple cartridge (see FIG. 10), the staple driver 61 is in a fired position and the staples has been fired from the staple cartridge. The firing bar 33 can engage with the staple driver 61 when moving distally, so as to move the staple driver 61 from the unfired position to the fired position and then fire the staples.

The end effector assembly 30 according to the present disclosure further comprises a lockout assembly 40 for locking both of the closure plates 32 and the firing bar 33 from advancing distally in the case of no staple cartridge being installed, or in the case of an incompatible staple cartridge or a spent staple cartridge being installed. The lockout assembly 40 is pivotally installed between the pair of closure plates 32 and can pivot between a locked position and an unlocked position. In the locked position, the lockout assembly 40 may prevent the pair of closure plates 32 and the firing bar 33 from advancing distally; and in the unlocked position, the lockout assembly 40 allows the pair of closure plates 32 and the firing bar 33 to advance distally.

FIG. 5 shows the end effector assembly 30 without any staple cartridge installed, in which the hook-shaped member 31 and the closure plate 32 on a side facing towards readers are omitted in order to show the lockout assembly 40. FIG. 5 and FIG. 6 show the lockout assembly 40 in the locked position. Referring to FIG. 6 to FIG. 8, the lockout assembly 40 comprises a lockout member 41 and a spring member 42, and a pivot 43 is fixed on and between the pair of closure plates 32 and the lockout member 41 is pivotally mounted between the pair of closure plates 32 via the pivot 43, wherein the spring member 42 is used to apply torque to the lockout member 41 to bias the lockout member 41 toward the locked position. The lockout member 41 comprises a first hook-shaped arm 411 extending distally and a second hook-shaped arm 412 extending proximally. When the lockout member 41 is in the locked position as shown in FIG. 6, the first hook-shaped arm 411 can prevent or block the firing bar 33 from advancing distally, and the second hook-shaped arm 412 engages with a pin or rivet 311 fixed between the pair of hook-shaped members 31 to prevent the pair of closure plates 32 from advancing distally. Specifically, the first hook-shaped arm 411 has an end which is upwardly curved, while the second hook-shaped arm 412 has an end which is downwardly curved. When the lockout member 41 is in the locked position as shown in FIG. 6, the end of the first hook-shaped arm 411 engages with the firing bar 33 to prevent the firing bar 33 from advancing distally, or is positioned on an advancing path of the firing bar 33 to block the firing bar 33 from advancing distally; and the end of the second hook-shaped arm 412 engages with the pin 311 to prevent the pair of closure plates 32 from advancing distally, or is positioned at a proximal side of the pin 311 to engage with the pin as the lockout member moving distally with the closure plates 32, so as to prevent the lockout member 41 and the pair of closure plates 32 from advancing distally. In an alternative embodiment, the first hook-shaped arm 411 may have an upwardly opening notch for receiving a corresponding portion of the firing bar 33 when in the locked position, and the second hook-shaped arm 412 may have a downwardly opening notch for receiving the pin 311 when in the locked position.

When the lockout member 41 rotates to the unlocked position (see FIG. 9), the first hook-shaped arm 411 disengages from the firing bar 33 or leaves the advancing path of the firing bar 33 so as to allow the firing bar 33 to advance distally, and the second hook-shaped arm 412 disengages from the pin 311 or is no longer positioned at the proximal side of the pin 311 so as to allow the lockout member 41 and the pair of closure plates 32 to advance distally.

FIG. 7 and FIG. 8 show specific structures of the lockout member 41 and the spring member 42. The lockout member 41 further comprises a stepped portion 413 formed between the first hook-shaped arm 411 and the second hook-shaped arm 412, wherein the spring member 42 biases the lockout member 41 towards the locked position through applying a pushing force to the stepped portion 413. Specifically, a distal-facing surface 42*a* of a first end (a lower end in FIG. 6 and FIG. 8) of the spring member 42 abuts against the stepped portion 413, and a second end of the spring member 42 may be fixed on any one of the hook-shaped members 31, the closure plates 32 and the firing bar 33. In order to deflect the spring member 42 to obtain an initial spring force, a proximal-facing surface 42*b* of a portion of the spring member 42 between two ends of the spring member 42 abuts against the pivot 43. The spring member 42 may further comprise a slot 42*c* extending in a longitudinal direction of the spring member 42, and the lockout member 41 passes through the slot 42*c* so that the first hook-shaped arm 411 is positioned at a distal side of the spring member 42 and the second hook-shaped arm 412 is positioned at a proximal side of the spring member 42. Those skilled in the art will appreciate that the spring member 42 may also be replaced by other spring members, such as a torsion spring, as long as they can apply torque to the lockout member 41.

The following describes in detail about how the lockout assembly 40 is unlocked by the staple cartridge. As described above, the pair of closure plates 32 may be used to hold the staple cartridge, and the staple cartridge may be installed between the pair of closure plates 32 along an installation direction L. According to the present disclosure, each side of the staple cartridge is provided with a protrusion 62 (see FIG. 2), and a slot 63 extending along the installation direction L, wherein positions and dimensions of the protrusions 62 and the slots 63 on different models of the staple cartridges may be different in order to prevent inappropriate installation. Correspondingly, each of tops of the pair of closure plates 32 of the surgical instrument according to the present disclosure is provided with a notch 321 respectively, and one or more ribs 322 extending along the installation direction L are respectively provided on an inner surface of each of the pair of closure plates 32, as shown in FIG. 3 and FIG. 5, wherein the closure plate 32 close to the reader side are omitted in FIG. 3.

Further referring to FIG. 4, after a compatible model of staple cartridge being installed in the surgical instrument, the protrusions 62 of the staple cartridge are received in the notches 321 of the surgical instrument, and the one or more ribs 322 of the surgical instrument are slidably received in the slots 63 of the staple cartridge, thereby enabling the staple cartridge to be installed in place in the surgical instrument and unlocking the lockout assembly 40. An incompatible model of staple cartridge cannot be installed in place in the surgical instrument, because the protrusions of such staple cartridge can't fit with the notches of the surgical instrument or the slots can't fit with the ribs of the surgical instrument, thereby the lockout assembly 40 cannot be unlocked.

FIG. 9 exemplarily shows a condition where an unused staple cartridge is installed in place in the surgical instrument and unlocks the lockout assembly, in which the hook-shaped member 31 and the closure plate 32 on the side facing towards the readers are omitted and a portion thereof is shown in a cross-sectional view in order to show the internal lockout assembly 40. As can be seen from FIG. 9, when the unused staple cartridge 60 of a compatible model is installed in place in the surgical instrument, a bottom end of the staple driver 61 in the unfired position can engage with the hook-shaped arm 411 of the lockout member 41 and downwardly push the hook-shaped arm 411, thus enabling the lockout member 41 to pivot about the pivot 43 to the unlocked position, after that, both the closure plates 32 and the firing bar 33 may advance distally.

From the above description, it can be known that the compatibility of shapes and dimensions (especially dimensions along the installation direction L) of the protrusions 62 of the staple cartridge with the notches 321 of the surgical instrument will affect that whether the staple cartridge can be installed in place in the surgical instrument and then unlock the lockout assembly 40. Therefore, the dimension of the notch 321 (especially the dimension along the installation direction L) is associated with the locked position and the unlocked position of the lockout member 41. In a preferred embodiment, the notch 321 has a substantially triangular profile, and one vertex of the triangular profile faces towards the installation direction L of the surgical staple cartridge 60.

FIG. 10 exemplarily shows a condition where a spent staple cartridge is installed in place in the surgical instrument, in which the hook-shaped member 31 and the closure plate 32 on the side facing towards the readers are omitted and a portion thereof is shown in a cross-sectional view in order to show the internal lockout assembly 40. As shown in the figure, when the spent staple cartridge 60 of a compatible model is installed in place in the surgical instrument, the staple driver 61 at the firing position is positioned at a distal side of the hook-shaped arm 411, and cannot engage with the hook-shaped arm 411, so the lockout assembly 40 cannot be unlocked, in this case, the closure plates 32 and the firing bar 33 are still locked by the lockout assembly 40 and can't distally advance.

The scope of protection of the present disclosure is defined only by the claims. References in this specification to "various embodiments", "some embodiments", "one embodiment" or "an embodiment" mean that specific features, structures or characteristics described in conjunction with the embodiments are included in at least one embodiment. Therefore, the phrases "in various embodiments", "in some embodiments", "in one embodiment" or "in an embodiment" and the like in the present specification are not necessarily all referring to the same embodiment. Furthermore, in one or more embodiments, the specific features, structures or characteristics may be combined in any suitable way. Therefore, without conflict, the specific features, structures or characteristics shown or described in conjunction with one embodiment can be fully or partially combined with the features, structures or characteristics of one or more other embodiments, and the resulting modifications and variations are also within the scope of the present disclosure.

We claim:

1. A surgical instrument, comprising:
a handle assembly;
a shaft assembly extending distally from the handle assembly; and
an end effector assembly coupled to the handle assembly via the shaft assembly, the end effector assembly being configured to be manipulated by the handle assembly to transit between an open configuration and a closed configuration, wherein the end effector assembly comprises:
a pair of hook-shaped members,
a pair of closure plates positioned between the pair of hook-shaped members, the pair of closure plates being configured to be manipulated by the handle assembly to advance distally to thereby convert the end effector assembly from the open configuration to the closed configuration,
a firing bar positioned between the pair of closure plates, the firing bar being configured to be manipulated by the handle assembly to advance distally, and
a lockout assembly, the lockout assembly being pivotally mounted on the pair of closure plates and positioned therebetween, the lockout assembly being configured to pivot between a locked position in which the lockout assembly is configured to prevent the pair of closure plates and the firing bar from advancing distally, and an unlocked position in which the lockout assembly is configured to allow the pair of closure plates and the firing bar to advance distally.

2. The surgical instrument according to claim 1, wherein the lockout assembly comprises:
a lockout member pivotably mounted between the pair of closure plates via a pivot, and
a spring member configured to bias the lockout member towards a locked position to thereby provide the lockout assembly in the locked position.

3. The surgical instrument according to claim 2, wherein the lockout member comprises a first hook-shaped arm extending distally and a second hook-shaped arm extending proximally,
wherein, when the lockout member is in the locked position, the first hook-shaped arm is configured to prevent the firing bar from advancing distally, and the second hook-shaped arm is configured to prevent the pair of closure plates from advancing distally; and
wherein, when the lockout member pivots to the unlocked position, the first hook-shaped arm is configured to allow the firing bar to advance distally, and the second hook-shaped arm is configured to allow the pair of closure plates to advance distally.

4. The surgical instrument according to claim 3, wherein the first hook-shaped arm has an end which is upwardly curved, and the second hook-shaped arm has an end which is downwardly curved,
wherein, when the lockout member is in the locked position, the end of the first hook-shaped arm is configured to engage with the firing bar or is positioned at a distal side of the firing bar to prevent the firing bar from advancing distally, and the end of the second hook-shaped arm is configured to engage with a pin fixed between the pair of hook-shaped members or positioned at a proximal side of the pin to prevent the pair of closure plates from advancing distally; and
wherein, when the lockout member is in the unlocked position, the end of the first hook-shaped arm is configured to disengage from the firing bar or is no longer positioned at the distal side of the firing bar so as to allow the firing bar to advance distally, and the end of the second hook-shaped arm is configured to disengage from the pin or is configured to no longer be positioned at the proximal side of the pin so as to allow the pair of closure plates to advance distally.

5. The surgical instrument according to claim 4, wherein the lockout member further comprises a stepped portion located between the first hook-shaped arm and the second hook-shaped arm, wherein a distal-facing surface of a first end of the spring member abuts against the stepped portion, and wherein a second end of the spring member is fixed at any one of the hook-shaped members, the closure plates and the firing bar, and wherein a proximal-facing surface of a portion of the spring member between the first end and the second end abuts against the pivot.

6. The surgical instrument according to claim 4, wherein the spring member has a slot extending in a longitudinal direction of the spring member, and the lockout member is adapted to pass through the slot such that the first hook-shaped arm is positioned distal to the spring member and the second hook-shaped arm is positioned proximal to the spring member.

7. The surgical instrument according to claim 3, wherein the pair of closure plates are configured to removably hold a surgical staple cartridge which comprises a staple driver configured to be pushed distally by the firing bar to move from an unfired position to a fired position, wherein, when the surgical staple cartridge is installed in place between the pair of closure plates along an installation direction of the surgical staple cartridge, the first hook-shaped arm is configured to be engaged by the staple driver in the unfired position to pivot the lockout member towards the unlocked position, and the first hook-shaped arm is configured to not engage with the staple driver in the fired position so as to keep the lockout member in the locked position.

8. The surgical instrument according to claim 7, wherein top ends of the pair of closure plates include respective notches, each notch being configured to receive a corresponding protrusion provided on a surgical staple cartridge which is compatible with the surgical instrument, to thereby allow the surgical staple cartridge to be installed in place between the pair of closure plates.

9. The surgical instrument according to claim 8, wherein a dimension of the notch along the installation direction of the surgical staple cartridge is associated with the locked position and the unlocked position of the lockout member.

10. The surgical instrument according to claim 8, wherein the notch has a substantially triangular profile, and wherein one vertex of the triangular profile faces towards the installation direction of the surgical staple cartridge.

11. The surgical instrument according to claim 7, wherein inner sides of the pair of closure plates include one or more ribs extending along the installation direction of the surgical staple cartridge, and the one or more ribs are configured to be received in corresponding slots provided on the surgical staple cartridge which is compatible with the surgical instrument.

* * * * *